(12) United States Patent
Kaneko

(10) Patent No.: US 10,687,695 B2
(45) Date of Patent: Jun. 23, 2020

(54) BENDING TUBE AND ENDOSCOPE APPARATUS INCLUDING BENDING TUBE

(71) Applicant: OLYMPUS CORPORATION, Hachioji-shi, Tokyo (JP)

(72) Inventor: Mitsuru Kaneko, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 382 days.

(21) Appl. No.: 15/441,017

(22) Filed: Feb. 23, 2017

(65) Prior Publication Data

US 2017/0156567 A1    Jun. 8, 2017

Related U.S. Application Data

(63) Continuation of application No. PCT/JP2015/074683, filed on Aug. 31, 2015.

(30) Foreign Application Priority Data

Sep. 17, 2014 (JP) ................. 2014-189363

(51) Int. Cl.
*A61B 1/008* (2006.01)
*A61B 1/005* (2006.01)
*A61B 1/00* (2006.01)

(52) U.S. Cl.
CPC ............ *A61B 1/008* (2013.01); *A61B 1/0011* (2013.01); *A61B 1/0055* (2013.01)

(58) Field of Classification Search
CPC .... A61B 1/0088; A61B 1/0011; A61B 1/0055

USPC .................................................. 600/141, 142
See application file for complete search history.

(56) References Cited

U.S. PATENT DOCUMENTS

| 2009/0209819 A1* | 8/2009 | Kitagawa ............. A61B 1/0055 600/142 |
| 2010/0004509 A1* | 1/2010 | Naito ................... A61B 1/0055 600/141 |
| 2010/0056868 A1* | 3/2010 | Kitagawa ............. A61B 1/0055 600/142 |
| 2014/0180009 A1 | 6/2014 | Tanii |

FOREIGN PATENT DOCUMENTS

CN    103764008 A    4/2014
EP    2732751 A1    5/2014
(Continued)

OTHER PUBLICATIONS

Nov. 24, 2015 Search Report issued in International Patent Application No. PCT/JP2015/074683.

(Continued)

*Primary Examiner* — Timothy J Neal
*Assistant Examiner* — William B Chou
(74) *Attorney, Agent, or Firm* — Oliff PLC

(57) ABSTRACT

A joint portion in the bending portion for use in the insertion portion of an endoscope joints bending pieces with slide surfaces parallel to the rotation axis of bending and with slide surfaces perpendicular to the rotation axis. Since the slide surfaces receive external force exerted in the direction of the rotation axis in a direction perpendicular to the surfaces, they are resistant to displacement or twisting.

7 Claims, 5 Drawing Sheets

(56) References Cited

FOREIGN PATENT DOCUMENTS

JP      2944533 B2    9/1999
WO   2013/084985 A1   6/2013

OTHER PUBLICATIONS

Oct. 11, 2017 Office Action issued in Chinese Patent Application No. 201580047959.3.
Mar. 21, 2017 International Preliminary Report on Patentability issued in International Patent Application No. PCT/JP2015/074683.

* cited by examiner

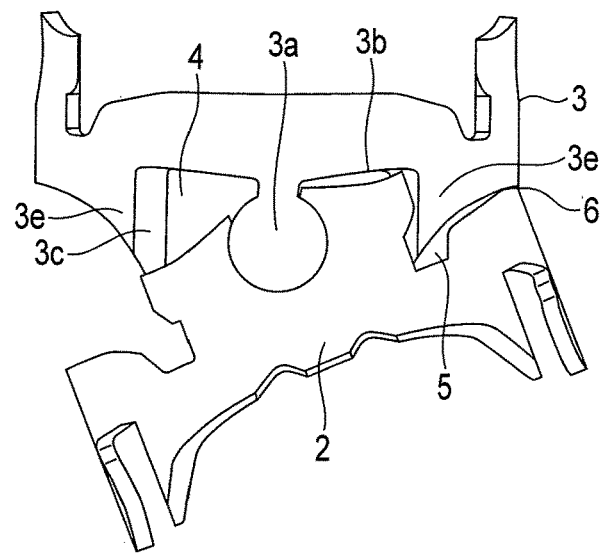
F I G. 4
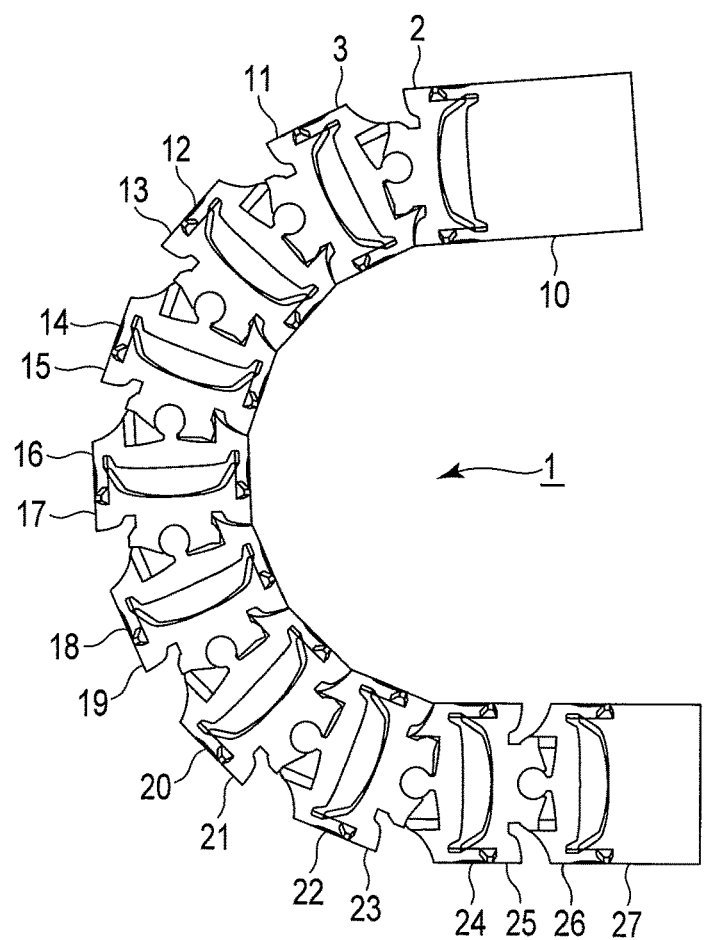
F I G. 5

BENDING TUBE AND ENDOSCOPE APPARATUS INCLUDING BENDING TUBE

CROSS-REFERENCE TO RELATED APPLICATIONS

This is a Continuation Application of PCT Application No. PCT/JP2015/074683, filed Aug. 31, 2015, which was published under PCT Article 21(2) in Japanese. This application is based upon and claims the benefit of priority from the Japanese Patent Application No. 2014-189363, filed Sep. 17, 2014, the entire contents of which are incorporated herein by reference.

BACKGROUND OF THE INVENTION

1. Field of the Invention

The present invention relates to an endoscope apparatus including a bendable bending tube to be provided on a distal end side of an inserting section.

2. Description of the Related Art

An endoscope apparatus to be inserted through a body cavity or a lumen for observing insides is generally known. An inserting section of an endoscope apparatus to be inserted through a body cavity or the like is configured to have a distal end portion that is freely bendable to move forward and backward along a bend in the body cavity, or to pick up an image of a part to be observed. The bending portion has a configuration in which a plurality of short bending pieces are jointed.

The bending pieces are connected to one another by wires, and can be freely bent by adjusting traction and relaxation of the wires by operating an angle knob of an operation section provided on a proximal end side.

When producing a bending portion, because of improvements in processing techniques, a link portion to be a rotation shaft of a joint portion and an engagement portion are simultaneously produced by making cuts in a straight tube with laser light. For example, Patent Literature 1: Japanese Patent No. 2944533 proposes a technique for making cuts in a straight tube with laser light toward a nearly central axis from a periphery of the tube, thereby forming bending pieces that are jointed to constitute a bending portion.

BRIEF SUMMARY OF THE INVENTION

According to an embodiment of the present invention, there is provided a bending tube comprising: a first bending piece to constitute a bendable bending tube; a second bending piece to rotate relative to the first bending piece; a link portion formed in the first bending piece and including a rotation axis for rotation of the second bending piece; an engagement portion which is formed in the second bending piece, which includes a slide surface that is nearly parallel to the rotation axis and that slides relative to the link portion, and which is rotatably engaged with the link portion; and a receiving portion which is formed near the link portion in the first bending piece, to which the engagement portion engaged with the link portion is contactable during rotation, and which has a perpendicular surface nearly perpendicular to the rotation axis.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 4 is an enlarged view of the mechanism of jointing the two bending pieces in a rotated state.

FIG. 5 is a diagram showing a bending tube that comprises a plurality of jointed bending pieces and that is bent in an up-down (UD) direction.

DETAILED DESCRIPTION OF THE PREFERRED EMBODIMENT

Embodiments will be described below with reference to the drawings.

First Embodiment

Figure 1:
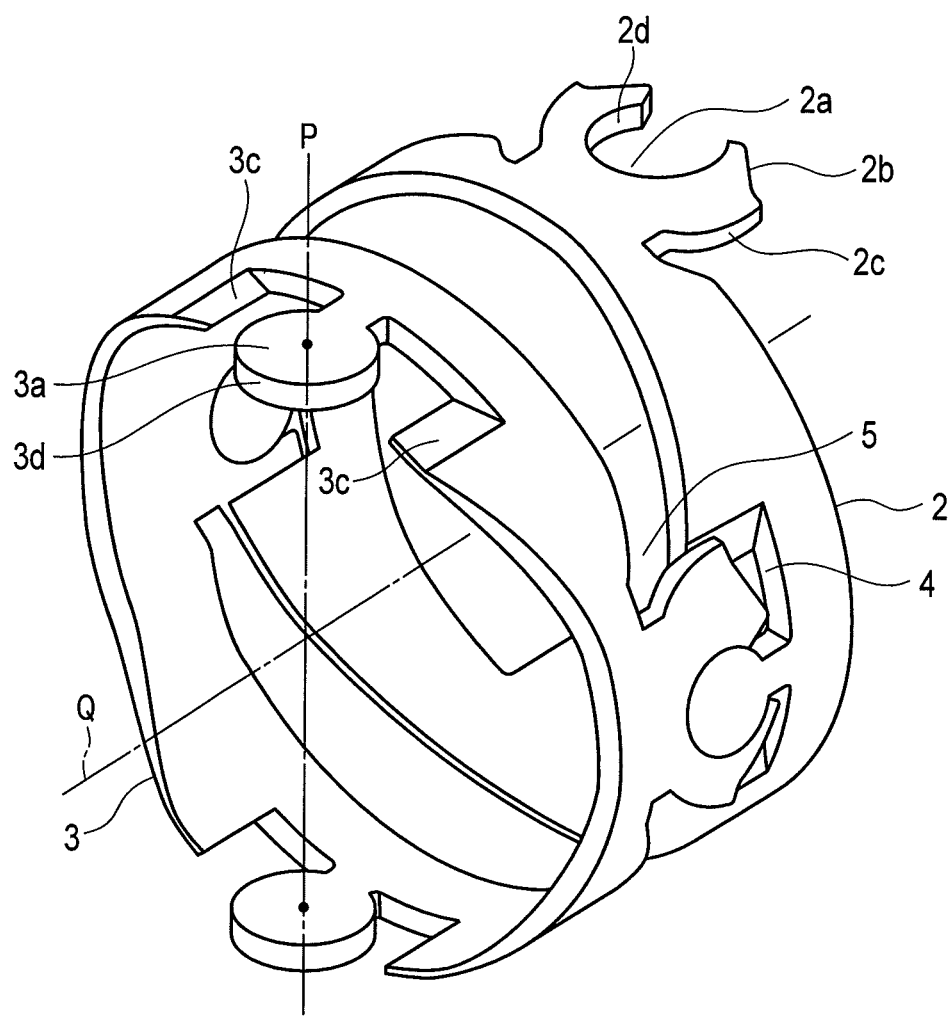
FIG. 1 is a view showing an external configuration of two jointed bending pieces in a bending tube of an inserting section of an endoscope apparatus according to a first embodiment of the present invention.
Figure 2:
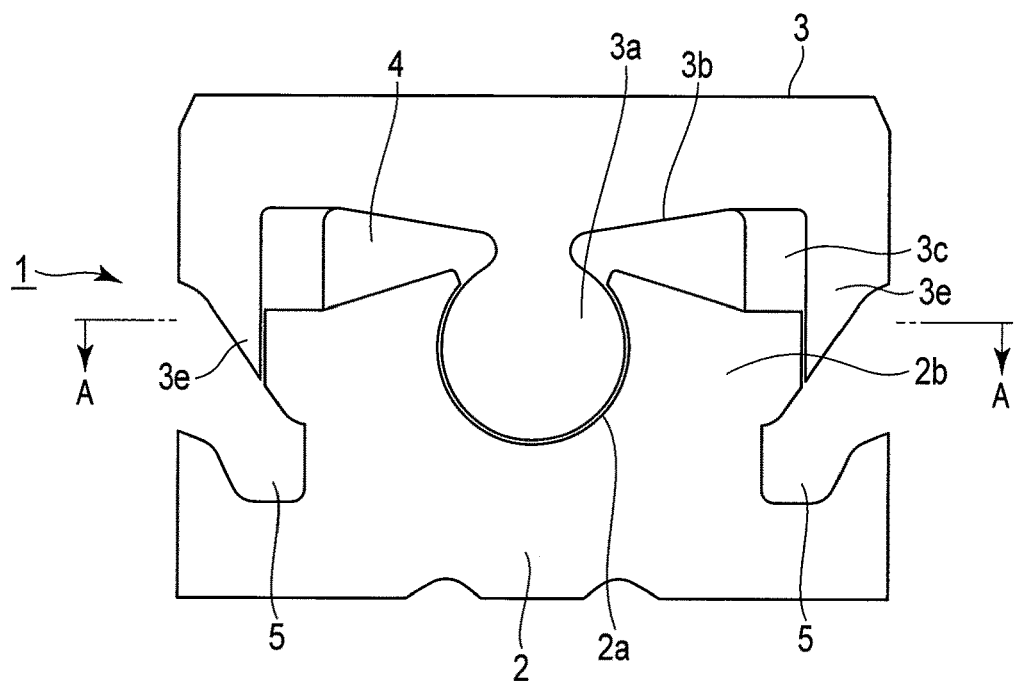
FIG. 2 is an enlarged view of a mechanism of jointing two bending pieces.
Figure 3:
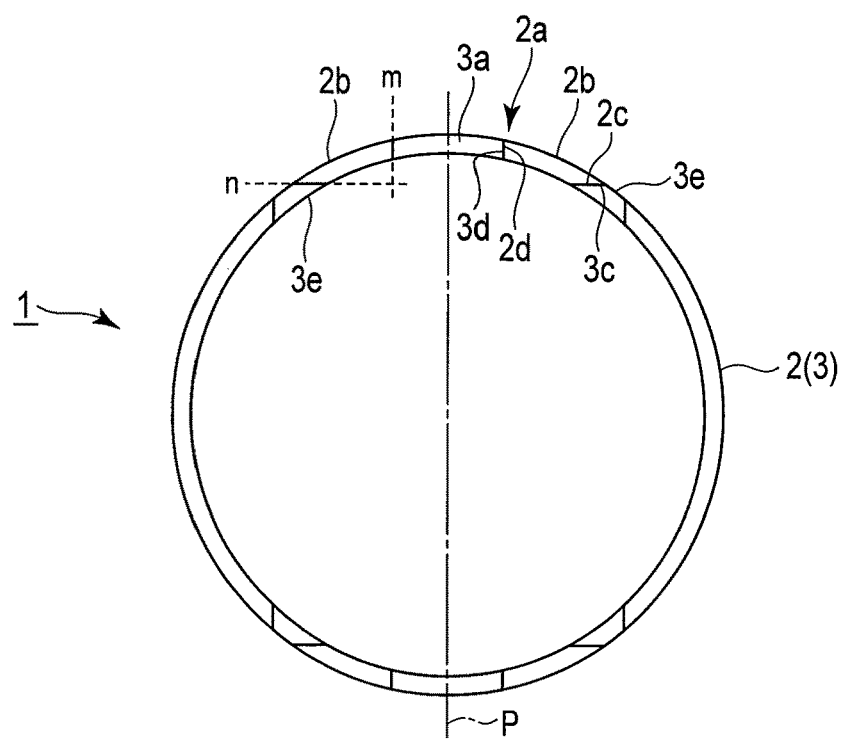
FIG. 3 is a cross-sectional view of a configuration of the bending pieces, taken along line A-A shown in FIG. 2.
Figure 6:
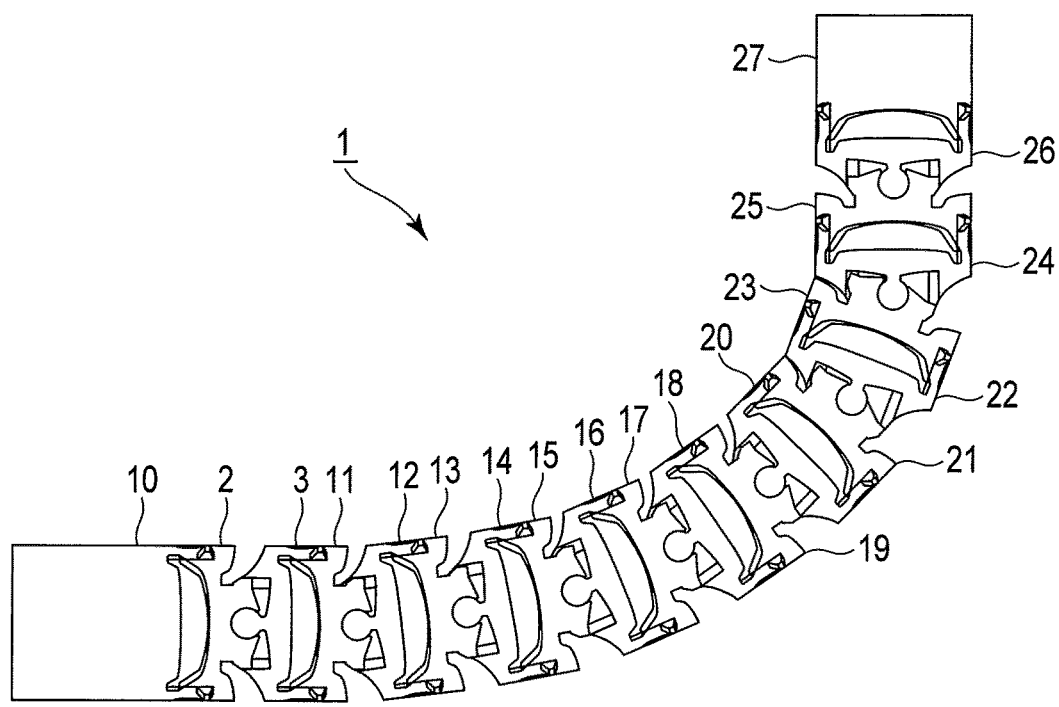
FIG. 6 is a diagram showing a bending tube that comprises a plurality of jointed bending pieces and that is bent in a right-left (RL) direction.

FIG. 1 is a view showing an external configuration of two jointed bending pieces in a bending tube of an inserting section of an endoscope apparatus according to the first embodiment of the present invention. FIG. 2 is an enlarged view of a mechanism of jointing two bending pieces. FIG. 3 is a cross-sectional view of a configuration of the bending pieces, taken along line A-A shown in FIG. 2. FIG. 4 is an enlarged view of the mechanism of jointing the bending pieces in a rotated state. FIG. 5 is a diagram showing a bending tube that comprises a plurality of jointed bending pieces and that is bent in an up-down (UD) direction. FIG. 6 is a diagram showing a bending tube that comprises a plurality of jointed bending pieces and that is bent in a right-left (RL) direction.

A bending tube of the inserting section according to this embodiment is formed by a laser machining technique of radiating a laser beam from outside to a hard pipe (made of SUS, NiTi, or the like) of a cylindrical straight tube to draw cuts. Alternatively, a wire-cut machining technique may be used.

In an example shown in FIG. 5, a bending tube 1 comprises a distal end bending piece 10, for example, 18 similar bending pieces 2, 3, and 11-26 (intermediate bending pieces), and finally, a proximal end bending piece 27, which are jointed to one another. In practice, these bending pieces are covered with a sheet member made of a rubber material or a resin material having stretch properties.

The bending tube is formed of the bending pieces with joint mechanisms to be described later, each joint mechanism formed of a link portion (first projection) and an engagement portion. Paired joint mechanisms are located at opposite sides of a central axis Q of the cylindrical bending pieces and the bending pieces are sequentially jointed in alternate arrangements of the joint mechanisms shifted by 90 degrees. The joints with the positions alternately shifted by 90 degrees make the bending pieces to be alternately bendable in an up-down direction and a right-left direction.

As shown in FIG. 1, a link portion 3a is formed a rounded projection (end portion). A pair of link portions are formed at opposite positions of the central axis Q of the cylindrical bending pieces on a distal side. Furthermore, a pair of projecting engagement portions 2b (second projections) are formed at opposite positions shifted by 90 degrees from the link portions 3a on a proximal side. With the joint of the plurality of bending pieces in this shape, the bending tube 1 can be bent in the up-down direction as shown in FIG. 5 and in the right-left direction as shown in FIG. 6 by pulling and loosening of wires (not shown). Naturally, in practice, the bending tube 1 can be bent in the up-down direction and the right-left direction in combination.

As shown in FIG. 2, the link portion 3a includes flat surfaces 3b, each extending with a falling gradient at 180 degrees or less from a support portion of the bending piece 3 in accordance with rotation angles of the bending pieces 2 and 3. Furthermore, on outer sides of the flat surfaces 3b, projecting receiving portions 3e including slide surfaces 3c that support the engagement portions 2b are provided.

A rotation axis P that is the center of rotation of the bending pieces 2 and 3 of this embodiment coincides with the center of the link portion 3a. In the configuration of this embodiment, a bending piece is in the maximum rotation state (the maximum rotation angle) when a shoulder tip portion 6 is brought into contact with the counterpart bending piece.

Furthermore, as shown in FIG. 2, end surfaces of both the engagement portions 2b are formed to extend also with a falling gradient outward. Triangular spaces defined by those flat surfaces 3b and the corresponding end faces are utilized as clearance rotation spaces 4 for the engagement portions 2b during rotation, as shown in FIG. 4. Similarly, both sides of the engagement portions 2b are recessed to provide concave shapes, and used as clearance rotation spaces 5 for the receiving portions 3e during rotation. Furthermore, a slide surface 2c to be described later is formed in a projection (a second projection) of the engagement portion 2b that is brought into contact with the slide surface 3c.

The link portion 3a and a cut 2a of a joint mechanism of this embodiment are fit to each other with a small gap therebetween, so that a slide surface 3d and a slide surface 2d in contact with each other (a first slide portion) are rotatable. The slide surfaces 2d and 3d are parallel to each other and formed in a direction m, which is nearly parallel to the rotation axis P, as shown in FIG. 3.

Similarly, the slide surface 3c and the slide surface 2c in the receiving portion 3e and the engagement portion 2b in contact with each other (a guide portion) are on a plane perpendicular to the rotation axis P, that is, a horizontal plane in a nearly horizontal direction n in FIG. 3. In a state where the bending pieces are linearly jointed, when the engagement portion 2b is rotated with respect to the link portion 3a, that is, when the slide surface 2d slides with respect to the slide surface 3d, the engagement portion 2b is brought into contact with the receiving portion 3e. In other words, the slide surface 2c slides with respect to the slide surface 3c.

With this configuration, as shown in FIGS. 1 and 4, if external force is exerted in a direction of the rotation axis P, the external force exerted on the engagement portion 2b is applied to the slide surface 3c of the receiving portion 3e via the slide surface 2c. The bending pieces are fully resistant to the external force, since the slide surface 3c receives the external force in a direction perpendicular to the surface direction. Similarly, if external force is exerted in a direction perpendicular to the rotation axis P, the bending pieces are fully resistant to the external force, since the external force is exerted in a direction perpendicular to the slide surface 3d and the slide surface 2d of the link portion 3a and the cut 2a.

Figure 8A:
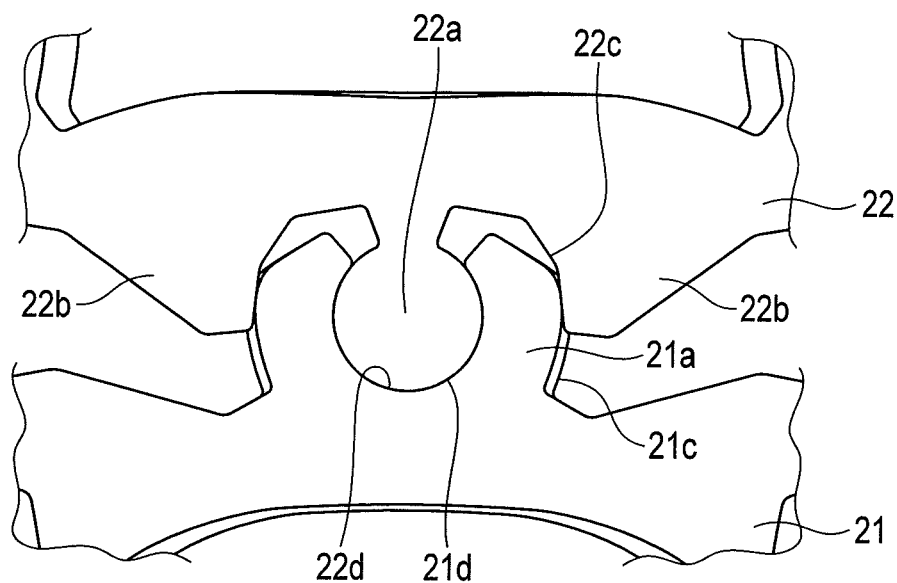
FIG. 8A is an enlarged view of a mechanism of jointing two conventional bending pieces.
Figure 8B:
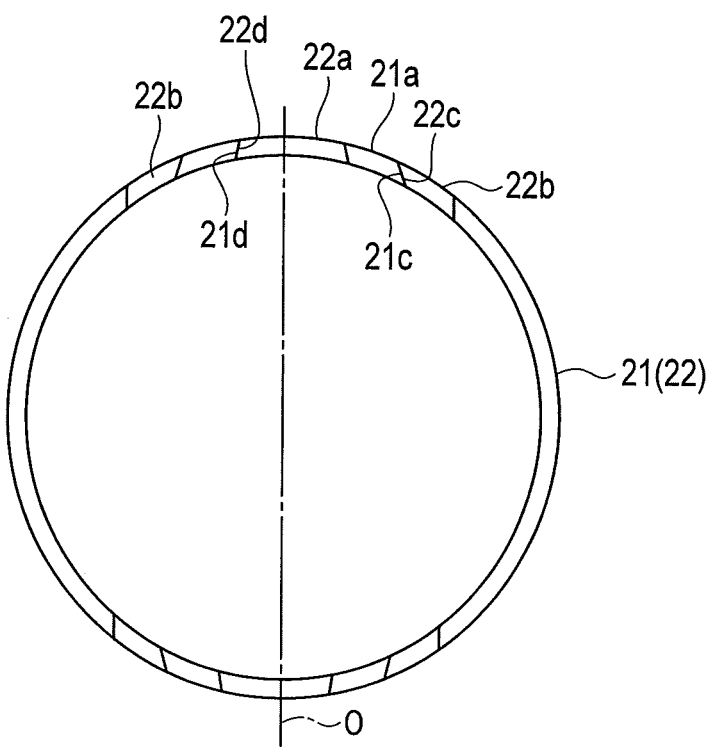
FIG. 8B is a cross-sectional view of a configuration of the bending pieces shown in FIG. 8A.

As shown in FIGS. 8A and 8B, according to the conventional art, the slide surfaces 21c and 22c of the engagement portion 21a and the receiving portion 22b are inclined relative to the direction of the rotation axis. Therefore, if external force is exerted in a direction of the rotation axis or a direction perpendicular to the rotation axis, the slide surfaces 21c and 22c receive the external force in a direction of shifting the surfaces obliquely relative to each other. Thus, the resistance of the prior art is lower than that of the embodiment in which external force is exerted in a direction perpendicular to the slide surfaces. As described above, according to the embodiment, displacement or jamming of the slide surfaces from or into each other can be avoided in the bending tube of the inserting section.

Second Embodiment

Figure 7:
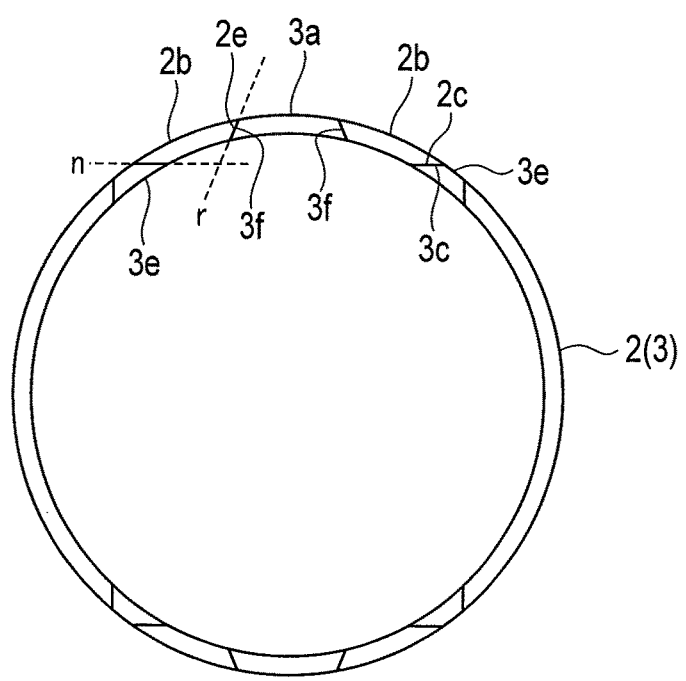
FIG. 7 is an enlarged cross-sectional view of a mechanism of jointing two bending pieces in an inserting section of an endoscope according to a second embodiment of the present invention.

FIG. 7 is an enlarged cross-sectional view of a mechanism of jointing two bending pieces of a bending tube in an inserting section of an endoscope apparatus according to the second embodiment. In the description of this embodiment, the structural parts equivalent to those of the first embodiment are identified by the same reference symbols as those used for the first embodiment, and detailed explanations thereof are omitted.

In the first embodiment described above, the slide surface 3d and the slide surface 2d of the link portion 3a and the cut 2a of the engagement portion 2b in the joint mechanism are formed in a direction parallel to the rotation axis P (shown in FIG. 3) and in a vertical direction m. In this embodiment, a slide surface 3f and a slide surface 2e (a second slide portion) have an inclination angle with respect to a rotation axis P.

Herein, the inclination is set to a direction r so that a diameter of an inner surface is larger than a diameter of an outer surface. The inclination may be set to a direction so that the diameter of the outer surface is larger than the diameter of the inner surface. Naturally, the slide surface 3c and the slide surface 2c in the receiving portion 3e and the engagement portion 2b in contact with each other are on a plane perpendicular to the rotation axis P, that is, in a horizontal direction n in FIG. 7.

This embodiment produces effects that the resistance to external force is equivalent to that of the first embodiment, and the link portion 3a is less likely to be displaced from the cut 2a because the slide surfaces 2e and 3f of the link portion 3a and the cut 2a in the engagement portion 2b (the second slide portion) are inclined.

The present invention can provide an endoscope apparatus comprising a bending tube having an increased resistance to external forces including pulling, bending, and twisting that act on a plurality of bending pieces formed by laser lithography cutting to connect with one another.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
an inserting section comprising a bending tube comprising:
   a first bending piece comprising:
     a link portion; and
     a receiving portion formed near the link portion and comprising a first slide surface; and
   a second bending piece configured to rotate relative to the first bending piece about an axis of rotation, the second bending piece comprising:
     an engagement portion rotatably engaged with the link portion and contactable with the receiving portion during rotation, the engagement portion comprising a second slide surface configured to slide relative to the link portion,
wherein:
   the axis of rotation extends through the link portion, and
   the first slide surface is approximately perpendicular to the axis of rotation, nearly parallel to a central axis of the first bending piece, and slidably engaged with the engagement portion during rotation.

2. The endoscope apparatus according to claim 1, wherein the second slide surface is inclined with respect to the axis of rotation.

3. The endoscope apparatus according to claim 2, wherein the first slide surface is nearly parallel to a central axis of the first bending piece.

4. The endoscope apparatus according to claim 2, wherein the bending tube comprises a plurality of the first bending pieces and a plurality of the second bending pieces.

5. The endoscope apparatus according to claim 1, wherein the bending tube comprises a plurality of the first bending pieces and a plurality of the second bending pieces.

6. An endoscope comprising:
an inserting section comprising a bending tube comprising:
   a first bending piece comprising:
     a link portion; and
     a receiving portion formed near the link portion and comprising a first slide surface; and
   a second bending piece configured to rotate relative to the first bending piece about an axis of rotation, the second bending piece comprising:
     an engagement portion rotatably engaged with the link portion and contactable with the receiving portion during rotation, the engagement portion comprising a second slide surface configured to slide relative to the link portion,
wherein:
   the axis of rotation extends through the link portion, and
   the first slide surface is approximately perpendicular to the axis of rotation and the second slide surface, and is slidable with respect to the engagement portion during rotation.

7. An endoscope comprising:
an inserting section comprising a bending tube comprising:
   a first bending piece comprising:
     a link portion; and
     a receiving portion formed near the link portion and comprising a first slide surface; and
   a second bending piece configured to rotate relative to the first bending piece about an axis of rotation, the second bending piece comprising:
     an engagement portion rotatably engaged with the link portion and contactable with the receiving portion during rotation, the engagement portion comprising a second slide surface configured to slide relative to the link portion,
wherein:
   the axis of rotation extends through the link portion, and
   the first slide surface is a tapered surface that is approximately perpendicular to the axis of rotation, and is slidable with respect to the engagement portion during rotation.

* * * * *